United States Patent
Hakozaki et al.

(10) Patent No.: US 8,524,204 B2
(45) Date of Patent: Sep. 3, 2013

(54) COSMETIC COMPOSITIONS AND METHODS FOR INHIBITING OR REDUCING TRYPSIN ACTIVITY

(75) Inventors: Tomohiro Hakozaki, Cincinnati, OH (US); Leo Timothy Laughlin, II, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/298,985

(22) Filed: Nov. 17, 2011

(65) Prior Publication Data

US 2012/0148515 A1 Jun. 14, 2012

Related U.S. Application Data

(60) Provisional application No. 61/415,632, filed on Nov. 19, 2010.

(51) Int. Cl.
*A61K 8/00* (2006.01)
*A61K 8/18* (2006.01)
*A61Q 19/02* (2006.01)

(52) U.S. Cl.
USPC .......................................................... 424/62

(58) Field of Classification Search
None
See application file for complete search history.

(56) References Cited

U.S. PATENT DOCUMENTS

| | | | |
|---|---|---|---|
| 3,755,560 A | 8/1973 | Dickert et al. | |
| 4,421,769 A | 12/1983 | Dixon et al. | |
| 5,550,166 A * | 8/1996 | Ostlund et al. | 514/715 |
| D391,162 S | 2/1998 | Kokenge | |
| 6,174,533 B1 | 1/2001 | Sanogueira | |
| D516,436 S | 3/2006 | Campbell et al. | |
| 7,054,674 B2 | 5/2006 | Cane et al. | |
| D535,191 S | 1/2007 | Corker | |
| D542,660 S | 5/2007 | Thomas et al. | |
| D547,193 S | 7/2007 | Blasko et al. | |
| D547,661 S | 7/2007 | Blasko et al. | |
| D558,591 S | 1/2008 | Blasko et al. | |
| D563,221 S | 3/2008 | Ashiwa et al. | |
| D570,707 S | 6/2008 | Blasko et al. | |
| 2004/0142853 A1 | 7/2004 | Patt | |
| 2004/0175347 A1 | 9/2004 | Bissett | |
| 2005/0019356 A1* | 1/2005 | Bissett et al. | 424/401 |
| 2005/0118119 A1 | 6/2005 | Stoltz | |
| 2006/0089553 A1 | 4/2006 | Cotton | |
| 2006/0275237 A1 | 12/2006 | Bissett | |
| 2007/0040306 A1 | 2/2007 | Morel et al. | |
| 2007/0203240 A1 | 8/2007 | Oblong et al. | |
| 2007/0205226 A1 | 9/2007 | Honda et al. | |
| 2008/0057015 A1 | 3/2008 | Oblong et al. | |
| 2008/0059313 A1 | 3/2008 | Oblong et al. | |
| 2009/0017080 A1 | 1/2009 | Tanner et al. | |
| 2010/0022461 A1* | 1/2010 | Cho et al. | 514/23 |
| 2010/0186669 A1 | 7/2010 | Shin et al. | |
| 2010/0189669 A1* | 7/2010 | Hakozaki | 424/60 |
| 2011/0045036 A1* | 2/2011 | Lintner et al. | 424/401 |
| 2011/0097286 A1* | 4/2011 | Swanson et al. | 424/59 |
| 2011/0183914 A1* | 7/2011 | Osborne | 514/18.8 |
| 2012/0148510 A1 | 6/2012 | Hakozaki | |
| 2012/0148515 A1 | 6/2012 | Hakozaki | |
| 2012/0156146 A1 | 6/2012 | Hakozaki | |

FOREIGN PATENT DOCUMENTS

| | | |
|---|---|---|
| DE | 19928112 | 12/2000 |
| EP | 1325737 | 7/2003 |
| EP | 1348438 A1 * | 10/2003 |
| EP | 1810614 A2 | 7/2007 |
| FR | 2913598 | 9/2008 |
| WO | WO 2008004788 A1 * | 1/2008 |
| WO | WO 2008101693 A2 * | 8/2008 |
| WO | 2010110863 A2 | 9/2010 |

OTHER PUBLICATIONS

Mintel Database "Youth Body Cream", Guinot, Jun. 2010, 5 pages http://www.gnpd.com.
Mintel Database Jan. 2010 "Neck and Decollete Care" 4 pages http://www.gnpd.com.
Mintel Database Jun. 2009."Moisturize Anti-Wrinkle Skin Firming Hydrator" April Rain Skin Science, 8 pages http://www.gnpd.com.
Mintel Database Apr. 2011. "Enriched Body Care" Mary Cohr. 5 pages http://www.gnpd.com.
Mintel Database "High Performance Hair Growth Stimulating Conditioner", DS Laboratories Feb. 2011, 5 pages http://www.gnpd.com.
Matts, P. et al., "Spectrophotometric Intracutaneous Analysis (SIAscopy)", 3rd Edition Handbook of Cosmetic Science and Technology, Paye, M., Barel, A.N. and Maibach, H.I. (eds), Informa Healthcare USA, Inc., New York, 275-283, 2008.
Matts, P., New Insights Into Skin Appearance and Measurement, Journal of Investigative Dermatology Symposium Proceedings (2008), 13, 6-9.
International Search Report; PCT Application No. PCT/US2011/061160; mailing date May 24, 2012; 14 pages.
International Search Report; PCT Application No. PCT/US2011/061167; mailing date Jun. 5, 2012; 14 pages.
International Search Report; PCT Application No. PCT/US2011/061159; mailing date May 24, 2012; 15 pages.
USPTO Office Action rejections/objections from co-pending U.S. Appl. No. 13/299,051, filed Nov. 17, 2011, Inventor Tomohiro Hakozaki, et al., Mail Date Sep. 26, 2012, 27 pages.
USPTO Office Action rejections/objections from co-pending U.S. Appl. No. 13/299,042, filed Nov. 17, 2011, Inventor Tomohiro Hakozaki, et al., Mail Date Sep. 26, 2012, 29 pages.

* cited by examiner

*Primary Examiner* — Robert A Wax
*Assistant Examiner* — Olga V Tcherkasskaya
(74) *Attorney, Agent, or Firm* — John G. Powell; Melody A. Jones

(57) ABSTRACT

A cosmetic composition formulated for topical application to skin is provided. The composition includes a safe and effective amount of cyclohexane-1,2,3,4,5,6-hexol; a safe and effective amount of an N-acyl amino acid compound; and a dermatologically acceptable vehicle.

13 Claims, 3 Drawing Sheets

COSMETIC COMPOSITIONS AND METHODS FOR INHIBITING OR REDUCING TRYPSIN ACTIVITY

CROSS REFERENCE TO RELATED APPLICATION

This application claims the benefit of U.S. Provisional Application Ser. No. 61/415,632 filed Nov. 19, 2010.

FIELD OF THE INVENTION

The present invention relates to cosmetic compositions and methods for inhibiting or reducing trypsin activity.

BACKGROUND OF THE INVENTION

Human skin comprises three principal layers: the epidermis, the dermis, and the subcutaneous fat layer. The epidermis comprises four layers (from top to bottom): the stratum corneum, the granular layer, the spiny layer, and the basal layer. A separate fifth layer, the stratum lucidum, may be present between the stratum corneum and granular layer. The basal layer produces cells which gradually migrate upward to form the other epidermal layers. As these cells migrate upward, they lose their central nucleus and start to produce skin proteins (keratins) and fats (lipids). These cells are known as keratinocytes when present in the upper layers of the epidermis. Melanocytes are another class of cells located in the basal layer of the epidermis. Melanocytes are responsible for the production of melanin, a pigment which is a primary factor in the tonal appearance of skin.

Referring to FIGS. 1, 2, and 3, melanin is produced by a complex set of reactions within the melanocyte involving, at a basic level, the enzyme tyrosinase and L-tyrosine as a substrate. Tyrosinase catalyzes the conversion of L-tyrosine to DOPA (L-3,4-dihydroxyphenylalanine) and of DOPA to dopaquinone. Dopaquinone undergoes further conversion to form melanin. Melanin aggregates in organelles known as the melanosomes which are transferred to keratinocytes along slender filaments of the melanocyte known as dendrites. The production of tyrosinase and its activity determine, in part, the amount of melanin produced. The amount and the type of melanin transferred to the keratinocytes determine, for their part, the degree of visual pigmentation of human skin.

One mechanism in the melanin production cycle is the transfer of melanosomes from the melanocytes to the keratinocytes by way of phagocytosis. Research has found that the protease-activated receptor 2 (PAR-2) expressed on keratinocytes is involved in melanosome transfer and therefore may regulate pigmentation. See, e.g., Seiberg, M. et al., *The Protease-Activated Receptor 2 Regulates Pigmentation via Keratinocyte-Melanocyte Interactions*, Experimental Cell Research 254, 25-32 (2000). Activation of PAR-2 with trypsin (or a trypsin-like protease) (or with the peptide agonist SLIGRL) initiates melanosome transfer, thereby contributing to the distribution of melanin within keratinocytes. In some cases, the distribution of melanin may manifest as an age spot or uneven skin tone. Compounds that inhibit trypsin (or a trypsin-like protease) activation of PAR-2 are believed to disrupt or reduce the phagocytosis of the melanocytes by the keratinocytes. Compounds that inhibit the PAR-2 either by inhibiting trypsin activity or by inhibiting SLIGRL peptide binding may regulate hyperpigmentation and melanin overproduction. See, e.g., Seiberg, M. et al., *The Protease-Activated Receptor 2 Regulates Pigmentation via Keratinocyte-Melanocyte Interactions*, Experimental Cell Research 254, 25-32 (2000).

In young skin, melanin is evenly distributed, and melanocyte activity is low, restricted to the production of constitutive pigmentation only. In aging skin, overzealous melanogenesis production and subsequent melanin transport can eventually create permanent local discoloration with sufficient size and contrast to appear as age spots (lentigines) or as diffuse hyperpigmentation or an uneven skin tone. Compositions and methods of treatment that minimize, reduce, ameliorate, or treat the size and/or contrast of age spots and/or which improve overall skin tone are continuing desires in the cosmetic field.

SUMMARY OF THE INVENTION

A cosmetic composition formulated for topical application to skin is provided. The composition comprises a safe and effective amount of cyclohexane-1,2,3,4,5,6-hexol; a safe and effective amount of an N-acyl amino acid compound; and a dermatologically acceptable vehicle.

In another embodiment, the cosmetic composition comprises a safe and effective amount of cyclohexane-1,2,3,4,5,6-hexol; a safe and effective amount of an N-acyl amino acid compound; a safe and effective amount of a vitamin B3 compound; a safe and effective amount of 2-hexyldecan-1-ol; and a dermatologically acceptable vehicle.

A cosmetic method for ameliorating, reducing or treating uneven skin tone or an age spot is also provided. The method comprises identifying a skin surface in need of such treatment; topically applying to the skin surface a cosmetic composition comprising a safe and effective amount of cyclohexane-1,2,3,4,5,6-hexol, a safe and effective amount of an N-acyl amino acid compound; and a dermatologically acceptable vehicle. The method may be repeated a sufficient number of times during a treatment period to ameliorate, reduce, or treat the uneven skin tone or age spot of the skin surface.

In response to the technical problems identified in the background, the present invention may take other forms. Further forms, of the present invention will be appreciated from the detailed description that follows.

BRIEF DESCRIPTION OF THE DRAWINGS

It is believed that the present invention will be better understood from the following description taken in conjunction with the accompanying drawings. The referenced drawings are not to be construed as limiting the scope of present invention.

DETAILED DESCRIPTION OF THE INVENTION

Figure 1:
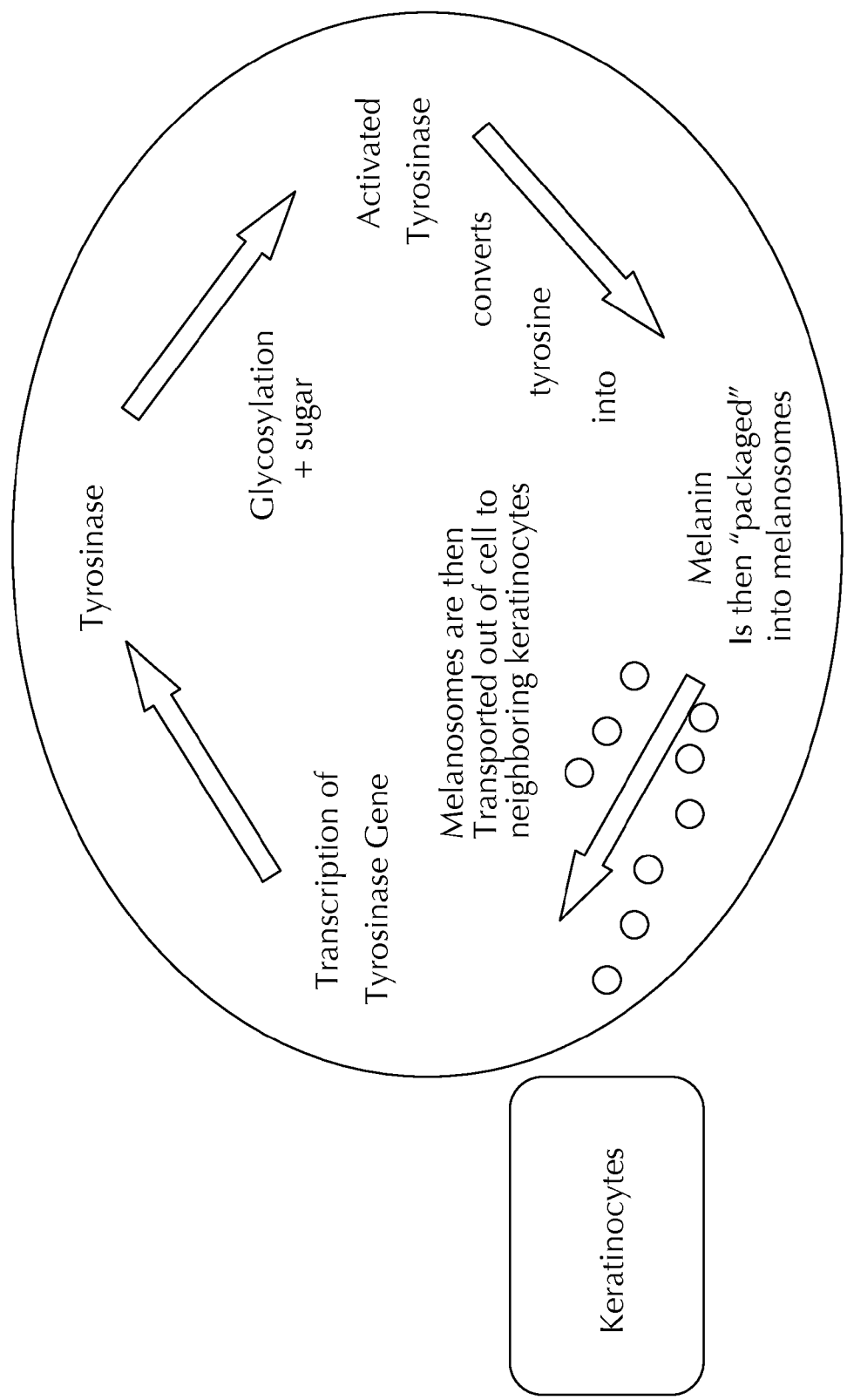
FIG. 1 is a schematic view of a melanin synthesis pathway.
Figure 2:
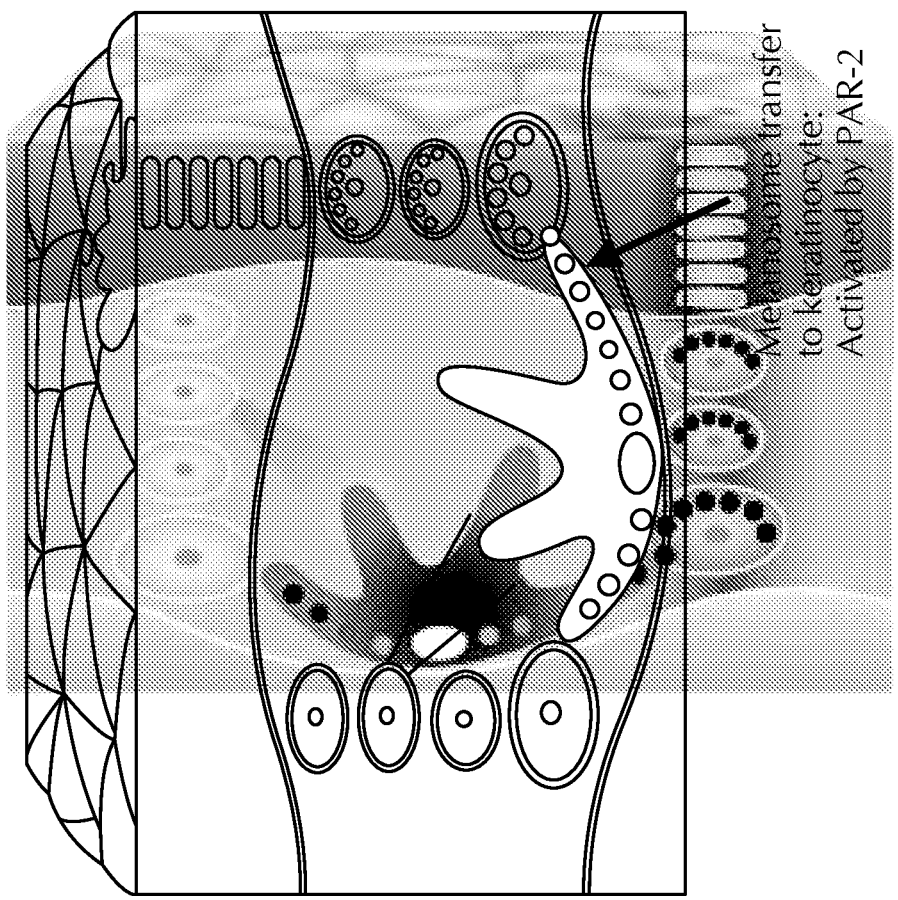
FIG. 2 is a schematic view of melanosome transport from a melanocyte to a keratinocyte along a dendrite.
Figure 3:
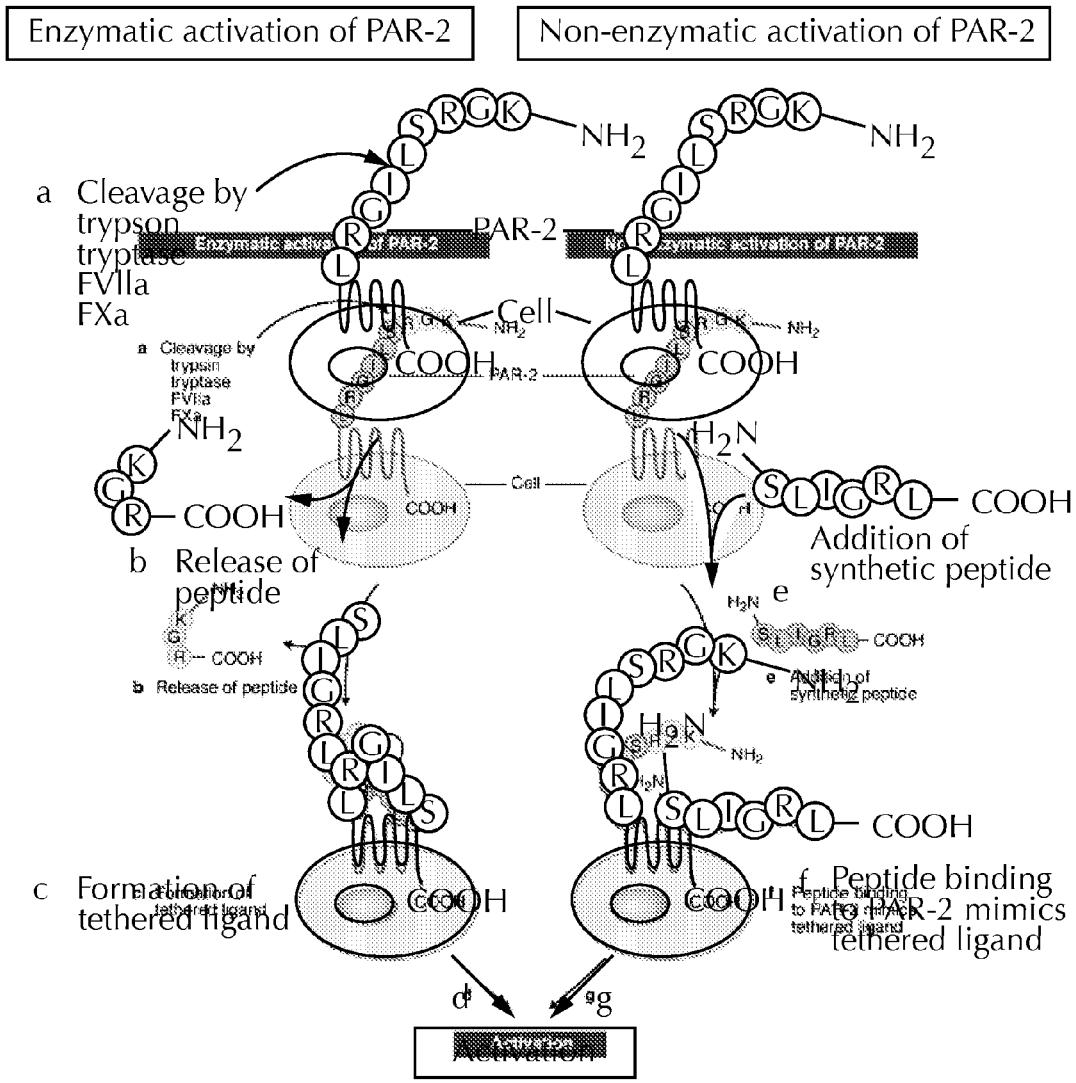
FIG. 3 is a schematic view illustrating the activation of the PAR-2 pathway.

All percentages and ratios used herein are by weight of the total composition and all measurements made are at 25° C., unless otherwise designated. All numeric ranges are inclusive of narrower ranges; delineated upper and lower range limits are interchangeable to create further ranges not explicitly delineated.

The compositions and methods of the present invention can comprise, consist essentially of, or consist of, the essential components as well as optional ingredients described herein.

As used herein, "consisting essentially of" means that the composition or component may include additional ingredients, but only if the additional ingredients do not materially alter the basic and novel characteristics of the claimed compositions or methods.

The term "apply" or "application", as used in reference to a composition, means to apply or spread the compositions of the present invention onto a human skin surface such as the epidermis.

The term "dermatologically acceptable," as used herein, means that the compositions or components described are suitable for use in contact with human skin tissue without undue toxicity, incompatibility, instability, allergic response, and the like.

The term "safe and effective amount" as used herein means an amount of a compound or composition sufficient to induce a positive benefit.

The term "age spot" as used herein refers to a defined area of skin wherein the pigmentation is greater than that of an adjacent area of skin due to localized and chronic or systemic overproduction/transport of melanin, typically caused by intrinsic and/or extrinsic aging. Age spots typically are between about 2 mm and about 10 mm in diameter but smaller or larger spots are possible. Age spots can include one or more of hyperpigmented spots, sun spots, solar lentigos, hypomelanotic lesions, freckles, and melasma spots.

The term "skin tone" as used herein refers to the overall appearance of melanin in the skin caused by the systemic, rather than transient, synthesis of melanin. Skin tone is typically characterized over a larger area of the skin. The area ideally may be than 100 mm$^2$, but larger areas are envisioned such as the entirety of the facial skin or any of the facial skin surfaces. Skin tone can be measured by image analysis. See, e.g., Matts, P., *New Insights Into Skin Appearance and Measurement*, Journal of Investigative Dermatology Symposium Proceedings (2008), 13, 6-9. For example, overall lightness can be measured by L* coordinate in L*a*b* color space (International Commission on Illumination). Chromophore mapping such as melanin mapping may be used as an indicator of overall skin tone. Mean melanin may be calculated from chromophore map data. Additionally, skin tone evenness can be determined by melanin which also may be determined calculated from the chromophore map data. See, e.g., Matts, P. et al., *Spectrophotometric Intracutaneous Analysis (SIAscopy)*, 3rd Edition Handbook of Cosmetic Science and Technology, Paye, M., Barel, A. N. and Maibach, H. I. (eds), Informa Healthcare USA, Inc., New York, 275-283, 2008; and EP 1810614; U.S. Pat. No. 7,054,674; and US 2006/0089553.

The term "facial skin surfaces" as used herein refers to one or more of forehead, periorbital, cheek, perioral, chin, and nose skin surfaces.

I. Compositions

Embodiments of the present invention comprise a combination of a N-acyl amino acid compound and cyclohexane-1,2,3,4,5,6-hexol and may optionally further comprise one or more of a vitamin B3 compound or 2-Hexyldecan-1-ol. The inventors have surprising discovered that a combination of a N-acyl amino acid compound and cyclohexane-1,2,3,4,5,6-hexol inhibit trypsin activity to a degree that is unexpectedly advantageous or superior to the compounds individually. The inventors have also surprisingly discovered that a combination of N-acyl amino acid compound, cyclohexane-1,2,3,4,5,6-hexol, a vitamin B3 compound, and 2-Hexyldecan-1-ol inhibit trypsin activity to a degree that is unexpectedly advantageous or superior to the compounds individually.

Compositions of the present invention may be made into a wide variety of product forms that include, but are not limited to, solutions, suspensions, lotions, creams, gels, toners, sticks, pencil, sprays, aerosols, ointments, pastes, foams, powders, mousses, shaving creams, wipes, strips, patches, adhesive bandages, hydrogels, film-forming products, facial and skin masks (with and without insoluble sheet), make-up such as foundations, eye liners, and eye shadows, and the like. The composition form may follow from the particular dermatologically acceptable carrier chosen, if present in the composition.

A. N-acyl Amino Acid Compounds

The compositions of the present invention comprise a safe and effective amount of one or more N-acyl amino acid compounds. The amino acid can be one of any of the amino acids known in the art. The N-acyl amino acid compounds of the present invention correspond to the formula:

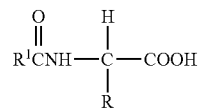

wherein R can be a hydrogen, alkyl (substituted or unsubstituted, branched or straight chain), or a combination of alkyl and aromatic groups. A list of possible side chains of amino acids known in the art are described in Stryer, *Biochemistry*, 1981, published by W.H. Freeman and Company. R$^1$ can be C$_1$ to C$_{30}$, saturated or unsaturated, straight or branched, substituted or unsubstituted alkyls; substituted or unsubstituted aromatic groups; or mixtures thereof.

Preferably, the N-acyl amino acid compound is selected from the group consisting of N-acyl Phenylalanine, N-acyl Tyrosine, their isomers, their salts, and derivatives thereof. The amino acid can be the D or L isomer or a mixture thereof. N-acyl Phenylalanine corresponds to the following formula:

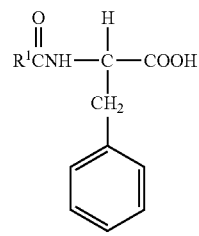

wherein R$^1$ can be C$_1$ to C$_{30}$, saturated or unsaturated, straight or branched, substituted or unsubstituted alkyls; substituted or unsubstituted aromatic groups; or mixtures thereof.

N-acyl Tyrosine corresponds to the following formula:

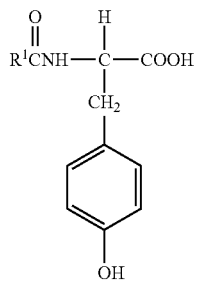

wherein $R^1$ can be $C_1$ to $C_{30}$, saturated or unsaturated, straight or branched, substituted or unsubstituted alkyls; substituted or unsubstituted aromatic groups; or mixtures thereof.

A particularly useful compound in the present invention is N-undecylenoyl-L-phenylalanine. This agent belongs to the broad class of N-acyl Phenylalanine derivatives, with its acyl group being a C11 mono-unsaturated fatty acid moiety and the amino acid being the L-isomer of phenylalanine. N-undecylenoyl-L-phenylalanine corresponds to the following formula:

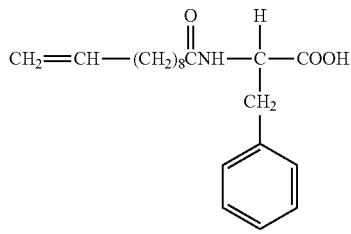

As used herein, N-undecylenoyl-L-phenylalanine is commercially available under the tradename Sepiwhite® from SEPPIC, France.

In the compositions of the present invention, the N-acyl amino acid may comprise greater than about 0.001%, 0.01%, or 0.2% and/or less than about 2% or 1% by weight of the composition.

B. Cyclohexane-1,2,3,4,5,6-hexol

The compositions of the present invention comprise a safe and effective amount of one or more cyclohexane-1,2,3,4,5, 6-hexol compounds that correspond to the following formula:

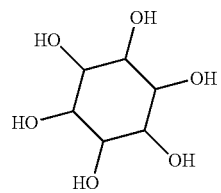 [SMILES: OC1C(O)C(O)C(O)C(O)C1O]

A particularly useful compound in the present invention is myo-inositol, sometimes referred to as Vitamin B8, having the following formula:

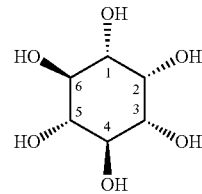

Myo-inositol is commercially available from the Sigma Chemical Company, Missouri, USA.

In the compositions of the present invention, the cyclohexane-1,2,3,4,5,6-hexol may comprise greater than about 0.001%, 0.1%, or 2% and/or less than about 5%, or 3% by weight of the composition.

C. Vitamin B3 Compounds

The compositions of the present invention may optionally comprise a safe and effective amount of one or more vitamin B3 compounds having the formula:

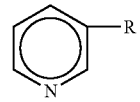

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid (e.g., tocopheryl nicotinate, myristyl nicotinate). Examples of suitable vitamin $B_3$ compounds are well known in the art and are commercially available from a number of sources (e.g., the Sigma Chemical Company, ICN Biomedicals, Inc., and Aldrich Chemical Company).

In the compositions of the present invention, the vitamin B3 compound may comprise greater than about 0.001%, 0.01%, 1% or 3% and/or less than about 10% or 5% by weight of the composition.

D. 2-Hexyldecan-1-ol

The compositions of the present invention comprise a safe and effective amount of 2-Hexyldecan-1-ol, commonly referred to as hexyldecanol. In the compositions of the present invention, 2-Hexyldecan-1-ol may comprise greater than about 0.001%, 0.01%, or 2.5% and/or less than about 10% or 5%, by weight of the composition.

In some embodiments, the ratio of N-acyl amino acid compounds to cyclohexane-1,2,3,4,5,6-hexol compounds in the cosmetic combination is between about 1:100 to about 10:1; or about 1:60 to about 2:1, or about 1:30 to about 1:1, or about 1:3.

In some embodiments, the ratio of N-acyl amino acid compounds to cyclohexane-1,2,3,4,5,6-hexol compounds to vitamin B3 compounds to 2-Hexyldecan-1-ol in the cosmetic combination is between about 0.2:2:5:5 and about 1:3:5:5, or between about 1:2:5:5 and about 1:3:5:5, or between about 0.2:3:5:5 and about 1:3:5:5.

E. Dermatologically Acceptable Carrier

The compositions of the present invention may also comprise a dermatologically acceptable carrier ("carrier") for the composition. The phrase "dermatologically acceptable carrier", as used herein, means that the carrier is suitable for topical application to the keratinous tissue, has good aesthetic properties, is compatible with the actives of the present and will not cause any safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be provided in a wide variety of forms. Non-limiting examples include simple solutions (aqueous or oil based), emulsions, and solid forms (gels, sticks, flowable solids, amorphous materials). In certain embodiments, the dermatologically acceptable carrier is in the form of an emulsion. An emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

The aqueous phase typically comprises water. However, in other embodiments, the aqueous phase may comprise components other than water (non-water components), including but not limited to water-soluble moisturizing agents, conditioning agents, anti-microbials, humectants and/or other water-soluble skin care actives. In one embodiment, the non-water component of the composition comprises a humectant such as glycerin and/or other polyols. However, it should be recognized that the composition may be substantially (i.e., less than 1% water) or fully anhydrous.

A suitable carrier is selected to yield a desired product form. Furthermore, the solubility or dispersibility of the compositions components (e.g., N-acyl amino acid compound, cyclohexane-1,2,3,4,5,6-hexol, vitamin B3 compound, and 2-Hexyldecan-1-ol) may dictate the form and composition of the carrier. In one embodiment, oil-in-water or water-in-oil emulsions are preferred.

Emulsions may further comprise an emulsifier. The composition may comprise any suitable percentage of emulsifier to sufficiently emulsify the carrier. Suitable weight ranges include from about 0.1% to about 10% or about 0.2% to about 5% of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421,769, and *McCutcheon's Detergents and Emulsifiers*, North American Edition, pages 317-324 (1986). Suitable emulsions may have a wide range of viscosities, depending on the desired product form.

The carrier may further comprise a thickening agent as are well known in the art to provide compositions having a suitable viscosity and rheological character.

II. Trypsin Assay Experiment

The following test method is provided to illustrate certain features and advantages of various embodiments of the present invention and should not be construed as limiting the scope thereof.

Trypsin from a bovine pancreas (available from Sigma-Aldrich, USA, Catalog #T8802) is diluted in phosphate buffered saline (PBS) to make a stock of about 0.001% trypsin. In a 96 well white plate with clear bottom (e.g., Corning Costar #3904 available from VWR International, LLC, Pennsylvania, USA), about 90 uL of 0.001% trypsin stock is mixed with about 10 uL of a test compound (e.g., N-undecylenoyl-L-phenylalanine) or vehicle control, such as dimethyl sulfoxide (DMSO) or water. Typically, there are 8 control wells per plate. The assay is initiated by the addition of 100 uL of the substrate, Z-Phe-Arg-7-amido-4-methylcoumarin (e.g., Calbiochem Catalog #03-32-1501-10 mM in PBS available from Life Technologies, California, USA) and the well plate is monitored in a fluorescent plate reader (e.g., a Gemini plate reader) with an excitation wavelength of 360 nm and an emission wavelength of 460 nm. The reaction progress is measured in a kinetic mode for 5 minutes. SoftMaxPro Data Analysis Software (available from Molecular Devices, Inc.) is used to fit a line to the data points for each well, and the slopes of the lines are then calculated. The slopes of each test compound well are compared to the average of the slopes of the vehicle control wells of a plate to determine the percentage of trypsin activity using equation (1) below. As the trypsin hydrolyzes the substrate, the fluorescence of the 7-amidocoumarin group increases, causing a growth in the signal which reflects the level of trypsin activity. An inhibitor attenuates the fluorescence growth resulting in a smaller slope.

$$\text{Percent}(\%)\text{trypsin activity}=[\text{slope of test well}]/[\text{average slope of vehicle control wells}] \quad (1)$$

Using generally the method outlined above, the percentage of trypsin activity was measured for 1:900 dilution of 1% N-undecylenoyl-L-phenylalanine, 3% myo-inositol, 5% niacinamide, and 5% hexyldecanol using a sample size of n=8 wells for each compound. The resulting percentages of trypsin activity are shown in Table 1 below.

TABLE 1

| A<br>N-undecylenoyl-L-phenylalanine<br>(% Activity) | B<br>Myo-Inositol<br>(% Activity) | C<br>Niacinamide<br>(% Activity) | D<br>Hexyldecanol<br>(% Activity) |
|---|---|---|---|
| 116.3 | 121.4 | 109.1 | 112.0 |
| 79.9 | 95.6 | 93.9 | 88.7 |
| 99.8 | 109.2 | 88.7 | 95.4 |
| 91.4 | 93.8 | 106.0 | 87.1 |
| 104.9 | 112.4 | 91.8 | 90.7 |
| 97.2 | 101.4 | 91.3 | 85.7 |
| 100.5 | 108.9 | 107.7 | 100.0 |
| 121.8 | 108.0 | 111.1 | 112.4 |

Using generally the method outlined above, the percentage of trypsin activity was also measured for 1:900 dilutions of four combinations of 1% N-undecylenoyl-L-phenylalanine, 3% myo-inositol, 5% niacinamide, and 5% hexyldecanol using a sample size of n=8 for each combination. The combinations were:

Combination #1=N-undecylenoyl-L-phenylalanine and Myo-Inositol.
Combination #2=N-undecylenoyl-L-phenylalanine; myo-inositol; and niacinamide.
Combination #3=N-undecylenoyl-L-phenylalanine; myo-inositol; and hexyldecanol.
Combination #4=N-undecylenoyl-L-phenylalanine; myo-inositol; niacinamide and hexyldecanol.

The resulting percentages of trypsin activity are shown in Table 2 below.

TABLE 2

| Combination #1<br>(A + B)<br>(% Activity) | Combination #2<br>(A + B + C)<br>(% Activity) | Combination #3<br>(A + B + D)<br>(% Activity) | Combination #4<br>(A + B + C + D)<br>(% Activity) |
|---|---|---|---|
| 50.2 | 76.8 | 57.5 | 34.0 |
| 35.3 | 59.1 | 45.7 | 29.5 |
| 45.1 | 57.3 | 44.0 | 34.2 |

TABLE 2-continued

| Combination #1 (A + B) (% Activity) | Combination #2 (A + B + C) (% Activity) | Combination #3 (A + B + D) (% Activity) | Combination #4 (A + B + C + D) (% Activity) |
|---|---|---|---|
| 45.7 | 72.8 | 35.7 | 29.0 |
| 47.1 | 61.1 | 39.1 | 38.7 |
| 44.8 | 65.2 | 42.8 | 30.8 |
| 46.6 | 71.1 | 42.8 | 29.0 |
| 62.9 | 69.2 | 47.2 | 32.4 |

Percentage values greater than 100% represent an up-regulation of trypsin activity while percentage values less than 100% represent a down-regulation (inhibition) of trypsin activity. As will be appreciated from Tables 1 and 2, the combination of N-undecylenoyl-L-phenylalanine and myo-inositol (combination #1) had a surprisingly unexpected or superior degree of trypsin inhibition compared to the individual compounds (e.g., A, B). The addition of niacinamide to combination #1 resulted in an increase in trypsin activity as compared to combination #1 while the addition of hexyldecanol to combination #1 resulted in similar trypsin activity to combination #1. Surprising, however, the addition of niacinamide and hexyldecanol (combination #4) to combination #1 resulted in the lowest level of trypsin activity (i.e., the highest level of trypsin inhibition).

III. Exemplary Compositions

The following are non-limiting examples of the compositions of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

Examples of some compositions are provided below.

| Component | Ex. A | Ex. B | Ex. C | Ex. D | Ex. E |
|---|---|---|---|---|---|
| Water | 62.58 | 61.25 | 63.58 | 62.25 | 71.25 |
| Glycerin | 10 | 10 | 10 | 10 | 10 |
| Disodium EDTA | 0.1 | 0.1 | 0.1 | 0.1 | 0.1 |
| Undeclenoyl Phenylalanine | 0.2 | 1 | 0.2 | 1 | 1 |
| Triethanolamine | 0.07 | 0.35 | 0.07 | 0.35 | 0.35 |
| Inositol | 3 | 3 | 2% | 2% | 3 |
| Tocopheryl Acetate | 0.5 | 0.5 | 0.5 | 0.5 | 0.5 |
| Isohexadecane | 3 | 3 | 3 | 3 | 3 |
| Isopropyl Isostearate | 1.33 | 1.33 | 1.33 | 1.33 | 1.33 |
| Sucrose Polycottonseedate | 0.67 | 0.67 | 0.67 | 0.67 | 0.67 |
| Hexyldecanol | 5 | 5 | 5 | 5 | 0 |
| Polyemthylsilsesquioxane | 0.25 | 0.25 | 0.25 | 0.25 | 0.25 |
| Cetearyl Glucoside, Cetearyl Alcohol | 0.5 | 0.5 | 0.5 | 0.5 | 0.5 |
| Behenyl Alcohol | 0.6 | 0.6 | 0.6 | 0.6 | 0.6 |
| Ethylparaben | 0.2 | 0.2 | 0.2 | 0.2 | 0.2 |
| Propylparaben | 0.1 | 0.1 | 0.1 | 0.1 | 0.1 |
| Cetyl Alcohol | 0.5 | 0.5 | 0.5 | 0.5 | 0.5 |
| Stearyl Alcohol | 0.7 | 0.7 | 0.7 | 0.7 | 0.7 |
| PEG-100 Stearate | 0.2 | 0.2 | 0.2 | 0.2 | 0.2 |
| Polyacrylamide (and) C13-14 Isoparaffine (and) Laureth-7 | 2.25 | 2.5 | 2.25 | 2.25 | 2.5 |
| Panethnol | 1 | 1 | 1 | 1 | 1 |
| Niacinamide | 5 | 5 | 5 | 5 | 0 |
| Benzyl Alcohol | 0.25 | 0.25 | 0.25 | 0.25 | 0.25 |
| Dimethicone and Dimethiconol | 2 | 2 | 2 | 2 | 2 |
| TOTAL | 100 | 100 | 100 | 100 | 100 |

The compositions of the present invention are generally prepared by conventional methods such as are known in the art of making compositions and topical compositions. Such methods typically involve mixing of the ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions are preferably prepared such as to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

IV. Methods of Treatment

Various methods of treatment may utilize the compositions of the present invention. In one embodiment, the method includes the step of identifying a skin surface comprising one or more age spots or uneven skin tone for treatment by the composition. The skin surface may be identified by the user or a third party such as a dermatologist, cosmetician, or other caregiver. Identification may be done by visual inspection of the skin surface in need of treatment based on size and/or color. Identification may also be done by commercially available imaging devices such SIAscope V (available from Astron Clinica, Ltd., UK) or the VISIA® Complexion Analysis system (available from Canfield Scientific, Inc., Fairfield, N.J.). Both devices are capable of collecting images of the skin and identifying age spots.

Skin surfaces of the most concern tend to be those not typically covered by clothing such as facial skin surfaces, hand and arm skin surfaces, foot and leg skin surfaces, and neck and chest skin surfaces (e.g., décolletage). In particular, identification of the age spot(s) and/or uneven skin tone of the facial skin surfaces includes the forehead, perioral, chin, periorbital, nose, and/or cheek skin surfaces.

The method may comprise the step of applying the composition to the skin surface, which may have been previously identified. Many regimens exist for the application of the composition. The composition may be applied at least once a day, twice a day, or on a more frequent daily basis, during a treatment period. The treatment period may vary. In one embodiment, the treatment period is between about 1 week and about 12 weeks. In another embodiment, the treatment period is between about 4 weeks and about 12 weeks. In yet another embodiment, the treatment period is between about 4 weeks and about 8 weeks. In certain embodiments, the treatment period will extend over multiple months (i.e., 3-12 months) or multiple years. In one embodiment the composition is applied least once a day during a treatment period of at least about 4 weeks or at least about 8 weeks. In another embodiment the composition is applied twice a day during a treatment period of at least about 4 weeks or 8 weeks. When applied twice daily, the first and second applications may be separated by at least 1 to about 12 hours. Typically, the composition may be applied in the morning and/or in the evening before bed.

The composition may be provided in a package sized to store a sufficient amount of the composition for the treatment period. The size, shape, and design of the package may vary widely. Some package examples are described in U.S. Pat. Nos. D570,707; D391,162; D516,436; D535,191; D542,660; D547,193; D547,661; D558,591; D563,221; 2009/0017080; 2007/0205226; and 2007/0040306.

The treatment period should be a sufficient time to provide an improvement in the skin surface. The improvement may be a detectable reduction in size of the age spot, lightening of the age spot (e.g., lighter in color), a decrease in melanin, or improvement in melanin evenness.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic composition formulated for topical application to skin, comprising:
   a safe and effective amount of cyclohexane-1,2,3,4,5,6-hexol;
   a safe and effective amount of an N-acyl amino acid compound; and
   a dermatologically acceptable vehicle, wherein the ratio of N-acyl amino acid compounds to cyclohexane-1,2,3,4,5,6-hexol compounds in the cosmetic combination is between about 1:100 and about 10:1.

2. The cosmetic composition of claim 1, wherein the concentration of cyclohexane-1,2,3,4,5,6-hexol is between about 2% and 3% by weight of the cosmetic composition.

3. The cosmetic composition of claim 1, wherein the N-acyl amino acid compound is undecylenoyl phenylalanine and the concentration of undecylenoyl phenylalanine is between about 0.2% and about 1% by weight of the cosmetic composition.

4. The cosmetic composition of claim 1, further comprising a vitamin B3 compound.

5. The cosmetic composition of claim 4, wherein the concentration of the vitamin B3 compound is between about 3% and about 5% by weight of the cosmetic composition.

6. The cosmetic composition of claim 4, wherein the vitamin B3 compound is niacinamide.

7. The cosmetic composition of claim 1, further comprising 2-hexyldecan-1-ol.

8. The cosmetic composition of claim 7, wherein the concentration of 2-hexyldecan-1-ol is between about 2.5% and about 5% by weight of the cosmetic composition.

9. A cosmetic composition formulated for topical application to skin, comprising:
   a safe and effective amount of cyclohexane-1,2,3,4,5,6-hexol;
   a safe and effective amount of an N-acyl amino acid compound;
   a safe and effective amount of a vitamin B3 compound;
   a safe and effective amount of 2-hexyldecan-1-ol; and
   a dermatologically acceptable vehicle, wherein the ratio of N-acyl amino acid compounds to cyclohexane-1,2,3,4,5,6-hexol compounds in the cosmetic combination is between about 1:100 and about 10:1.

10. The cosmetic composition of claim 9, wherein the N-acyl amino acid compound is undecylenoyl phenylalanine and the concentration of undecylenoyl phenylalanine is between about 0.2% and about 1% by weight of the cosmetic composition.

11. The cosmetic composition of claim 9, wherein the concentration of cyclohexane-1,2,3,4,5,6-hexol is between about 2% and about 3% by weight of the cosmetic composition.

12. The cosmetic composition of claim 9, wherein the concentration of the vitamin B3 compound is between about 3% and about 5% by weight of the cosmetic composition.

13. The cosmetic composition of claim 9, wherein the concentration of 2-hexyldecan-1-ol is between about 2.5% and about 5% by weight of the cosmetic composition.

* * * * *